United States Patent [19]

De Roeck born Holtzhauer et al.

[11] 4,029,760
[45] June 14, 1977

[54] ANTI-GINGIVITIS ORAL COMPOSITION

[75] Inventors: Yannick De Roeck born Holtzhauer; Herve De Roeck, both of Nantes, France

[73] Assignee: Agence Nationale de Valorisation de la Recherche (ANVAR), France

[22] Filed: Mar. 11, 1975

[21] Appl. No.: 557,353

[30] Foreign Application Priority Data

Mar. 12, 1974 France .............................. 74.09003

[52] U.S. Cl. .............................. 424/48; 424/180; 252/316; 426/575; 424/49
[51] Int. Cl.² .......................................... A61K 9/68
[58] Field of Search ....................... 424/49, 158, 48

[56] References Cited

UNITED STATES PATENTS 3,175,942  3/1965  Anderson et al. .................. 424/158

OTHER PUBLICATIONS

Watson, C. A. "Synthetic hydrocolloids and Dentifrices" J. Soc. Cosmet. Chem. vol. 21, 1970, pp. 459–470.
Moirano, A. L. "Degraded . . . containing Same" Chem. Abst., vol. 82, 1975, p. 403, para. 84784n.

*Primary Examiner*—Lewis Gotts
*Assistant Examiner*—Cary Owens
*Attorney, Agent, or Firm*—Berman, Aisenberg & Platt

[57] ABSTRACT

There are described pharmaceutical compositions useful for the treatment of gingivitis. Such a composition contains, as active ingredient from 0.5 to 25% by weight of at least one carraghenin in combination with a suitable vehicle. The compositions, which may contain various auxiliary components, can be in the form of toothpaste, mouthwash and like products. Even a short, but regular, use of a toothpaste containing the aforesaid composition results in a substantial improvement of gums and dental surfaces.

19 Claims, No Drawings

ANTI-GINGIVITIS ORAL COMPOSITION

This invention relates to a dentifrice, pharmaceutical or other composition for oral use to control gingivitis; it relates further to a method for obtaining such a composition as well as therapeutic applications thereof.

Inflammation of gums or "gingivitis" is an extremely widespread disease; it usually starts by a papillar irritation, followed by inflammation of marginal gum sections and finally by an attack of attached gum. This inflammation may later cause a bone lysis visible upon radiography or formation of supra- or infra- osseous pockets.

The origins of gingivitis are numerous, it may be caused by infectious diseases, drug intoxication or accidental intoxication, metabolic circulatory factors of nervous character leading to a brittlement of the gums. The most commonly occurring gingivitis is the so-called tartaric gingivitis which is due to accumulation on teeth of plaque and tartar.

Various tyrothricin-salt based toothpastes, most frequently in association with an anti-biotherapic oral treatment, are presently used to control gingivitis.

The applicants have now discovered a novel oral pharmaceutical composition providing an efficient control of gingivitis. For the purpose of this disclosure, the term "gingivitis" includes all kinds of gum inflammation without bone affliction, such an affliction being only curable by surgical means.

The oral pharmaceutical composition, according to the invention, useful against gingivitis, contains as active ingredient, at least one carragheenin in combination with a pharmaceutically-acceptable carrier.

The composition according to the invention may be in different forms, for instance in the form of toothcreams, toothpastes, liquid dentifrices, tooth-powders chewing-gum, tablets and the like.

It has been found according to the invention that carragheenins, and especially iota, kappa and lambda-carragheenins, used as active ingredients in oral pharmaceutical compositions, are endowed with an anti-inflammatory activity and are especially efficient against gingivitis.

Carragheenins are highly depolymerised derivatives of carragheenans, the later being extracts of various Floridea algae (Rhodophycea) belonging to the genera, Gelidium, Chondrus, Polyides, Gigartina. The most known carragheenans are lambda-, kappa, iota-, mu and nu-carragheenans, which are, in particular, described in "Handbuch der Kosmetika und Riechstoffe" H. Janistyn Dr. Alfred Huthig Verlag Heidelberg, 1969, pp 181 and 182. The average molecular weights of carragheenans is between 100,000 and 1,000,000.

On the contrary, the molecular weight of carragheenins which, like the carragheenans, are polygalactose ester-sulfates, is much lower; this molecular weight is lower than 100,000 and generally about 30,000.

There exist several carragheenins having various contents of sulfate groups per molecular unit; these are, in particular, lambda carragheenin, iota carragheenin and kappa carragheenin; these carragheenins have various I.R. spectra; in this connection reference can be made to the article entitled: "Structures and properties of some natural hydrocolloids" by G. BRIGAND in "PARFUMS, COSMETIQUES ET SAVONS DE FRANCE" (vol. 2 No10 octobre 1972), which relates to characterizing of carragheenans; it is believed that the same type of characterizing method can be applied for carragheenin characterization; said article being incorporated herein be reference.

It is known that carragheenans are often used in dentifrices as thickeners or in emulsions or suspensions as stabilisers (seen in this connection the article "Excipients d'origine algosique en cosmetologie et en dermopharmacie" by Y. de Roeck-Holtzhauer in "LA FRANCE ET SES PARFUMS" No. 68 - March-April 1970); see also U.S. Pat. No. 2,751,328.

It is further known that carragheenin has antipeptic properties and is useful for the treatment of gastrointenstinal ulcer. U.S. Pat. No. 3,175,942 discloses a pharmaceutical composition in the form of dose units comprising (a) "degraded" carragheenin having a sulfate content of about 28 to 32%, a molecular weight of less than 20,000, and a rotatory power of $+33°$ and (b) an anti acid agent. On this subject there also may be mentioned works of Lambelin in "Med. Pharmacol. exp." 14, pp 136 to 144 (1966) and Lambelin et al in "Gastroenterologia" 106, pp 13–24 (1966).

It has now been found according to the invention that a new pharmaceutical composition containing one or more carragheenins, as active ingredient, is efficient for controlling gingivitis.

Compositions which are the subject matter of the invention comprise, accordingly, as already stated, from about 0.5 to 25% by weight, preferably 0.5 to 10% of at least one carragheenin in combination with a pharmaceutically-acceptable carrier of the type currently used in compositions adapted to treat the oral cavity.

The compositions of the invention can also contain flavoring, colouring agents, sweeteners, preservatives, surface active agent and the like.

The pharmaceutically-acceptable carriers, useful in a composition of the invention, are chosen from currently-used vehicles for oral compositions, providing they are compatible with the carragheenin or carragheenins.

According to one embodiment of the invention, the antigingivitis composition is in the form of a dental composition and, mainly, in addition to the active ingredient, an abrasive component, a surface-active agent, a thickener, a sweetener, a flavoring agent, a preservative a wetting agent and, optionally, fillers; the aforesaid components, as well as others, are incorporated into the compositions of the invention in amounts which provide a composition having the desired consistency and the properties usually required in compositions of that kind.

The dentifrice composition according to the invention is preferably in the form of a tooth-paste.

According to an alternative embodiment, the dentifrice composition may be, for instance, in the form of liquid dentifrice, of a "dental milk", i.e., an oil-in-water-emulsion, a tooth-powder or any other suitable dentifrice composition.

According to a further embodiment of the invention, the composition can be in the form of mouthwash solutions, chewing-gums and the like.

One skilled in the art will be perfectly capable of determining the respective amounts of various components to be used for preparing a dental composition in the desired form.

Carragheenins suitable herein are those previously described, including iota, lambda, and kappa carragheenins and mixtures thereof. Advantageously, there can be used the product sold under the Trade name "AUBYGUM SD" which is a depolymerized extract of red algae of genus Gigartinacea, plentifully available on European and American coasts, which is of very high purity; this polysaccharide sulfate is in the form of an odourless and tasteless white powder; this product is a iota carragheenin.

Carragheenins used in compositions of the invention are free of toxicity, as shown by the work of already-cited Lambelin et al. The product "AUBYGUM SD" is sold by PIERREFITTE-AUBY (France).

The surface-active agent useful in the present compositions are cationic, non-ionic or other currently used surfactants suitable for dental compositions; examples of such compounds include sodium lauryl-sulfonate, ammonium lauryl-sulfonate, sodium or ammonium N-lauryl-sarcosinate and sodium lauryl-sulfoacetate.

The abrasive agent used herein must provide the composition with an abrasive power sufficient to remove bacterial plaque and nicotine stains; however, said agent should not be sufficiently powerful to scratch teeth and damage dental prostheses. Examples of suitable abrasive agents, include precipitated calcium carbonate, sodium metaphosphate, tricalcium phosphate, aluminum hydroxide, silica and bentonite.

It is necessary to incorporate at least one wetting agent in the toothpaste of the invention to avoid its hardening by exposure to air; as examples of such agent, one may cite sorbitol, propyleneglycol and glycerine. Another wetting agent commonly used in this field can alternatively be employed in the composition of the invention, providing it is compatible with the other components.

In the present specification the term "thickener" designates an agent which increases the viscosity of the composition.

As thickeners usable in the composition herein there will be mentioned gums, such as tragacanth gum, carragheenans, e.g., the product known as "AUBYGUM $X_2$" (Pierrefitte Auby), cellulose derivatives, such as carboxymethylcellulose, and alginates.

The sweetener used in the composition of the invention should be a non-fermentable product; saccharine is used to advantage; obviously, any other sweetener can be used for this purpose in the composition of the invention.

It is preferred to incorporate into the composition a preservative in order to protect the composition against any bacterial proliferation; this protection is one of the measures adapted to prevent any contamination of the product in the course of the manufacturing thereof. Suitable preservatives include methyl- propyl-, ethyl-, sodium- or ammonium-parahydroxybenzoate and phenolic compounds, such as phenol, m-cresol, p-cresol or thymol.

The composition of the invention advantageously contains flavoring agent adapted to give a pleasant flavor when brushing teeth. Suitable flavoring agents for the invention include the oils commonly used in dental compositions, such a peppermint oil, mandarin oil, apple oil, orange oil, strawberry oil and the like.

The compositions of the invention can also contain a filler, such as wheat starch.

With respect to dental milks, i.e., oil-in-water emulsions, the active ingredient, i.e., carragheenin, is dissolved in the aqueous phase; the oil suitable for this purpose can be a vegetable oil, e.g., of sweet-almond type or petrolatum oil. Emulsifiers comprise, e.g., polyoxyethylenic derivatives of fatty acid semiesters, such as the known products sold under Trade names "SPAN" and "TWEEN".

An especially preferred composition according to the invention is a tooth-paste composition which contains by weight about:
  0.5 to 10% of carragheenin
  0.5 to 2% of carragheenan
  2 to 4% of sorbitol
  25 to 35% of light $CaCO_3$ (powdery $CaCO_3$)
  2 to 4% of wheat starch
  1 to 3% of Na laurylsulfonate or $NH_4$-laurylsulfonate
    about 0.1% of saccharine about 0.1% of methyl-parahydroxybenzoate
  10 to 20% of glycerin
the balance to 100% being water and the amount of flavoring agent being 20 drops, especially of peppermint oil.

The viscosity of such compositions is generally in the range of from 20,000 to 30,000 centipoises.

The process for obtaining the above preferred tooth paste advantageously comprises the step of beating carragheenin, carragheenan and about 50% of the water to obtain a gel and successively adding $CaCO_3$, glycerin, the surface active agent, saccharine, methyl parahydroxybenzoate, wheat starch, sorbitol and water in a suitable manner to obtain a homogeneous mixture; when the flavoring agent is water-insoluble, it is added to the composition with the $CaCO_3$ or the wheat starch.

One skilled in the art will be able to prepare, without difficulty, a dentifrice composition (different from a tooth-paste) by mixing the components in sufficient amount to obtain the desired consistency. The composition of the invention is effective, as already mentioned to control gingivitis; accordingly, the invention has for a further object a method of treatment of gingivitis, which comprises applying to oral cavity and, specifically, to dental surfaces an effective amount of the composition of the invention for a time sufficient to establish an intimate contact therewith.

It is especially advantageous to brush teeth with a composition of the invention. Indeed, if the main purpose of teeth brushing is to remove all foreign coats, exogenous films, dental plaque, tartar covering the crowns and the like, such brushing also aims to exert in the gum area a slight massage action (likely depending on the type of brushing) and, on the other hand to exert a detergent action on desquamation coats.

Thus, with a composition according to the invention, it is possible to obtain a substantial improvement of the state of gums afflicted with gingivitis after a few days. It has been noted that the papillary, marginal attached index, i.e., the P.M.A. index (cf., on this subject, SCHOUR and MASSLER in "Gingivitis in Young adult males: Lack of effectiveness of permissive program of Tooth brushing," J. Periodant., 1957–28, 111–124), decreases to a great extent in a few days when using the composition of the invention, as illustrated by pharmacological tests described hereafter.

The invention will now be illustrated by the following examples given merely by way of an explanation and without any intent to limitation.

EXAMPLE I

In this example, there have been prepared dentifrice compositions of the invention in the form of toothpastes; the carragheenin weight content is respectively, 0.5% [composition A], 1% [composition B] and 2%

[composition C]; for this purpose, the carragheenin is a product sold under the trade name "AUBYGUM SD". All used components have been previously subjected to strict bacteriological controls.

Each prepared composition contains the following components in amounts shown in table I hereunder.

TABLE I

Antigingivitis dentifrice compositions of the invention

| Components | Composition A | B | C |
|---|---|---|---|
| carragheenin | 0.5 | 1 | 2 |
| carragheenan | 0.72 | 0.69 | 0.6 |
| light $CaCO_3$ | 30 | 30 | 30 |
| glycerin | 14.5 | 14.5 | 14.5 |
| ammonium laurylsulfonate | 2.35 | 2.35 | 2.35 |
| saccharine | 0.1 | 0.1 | 0.1 |
| methylparahydroxybenzoate | 0.1 | 0.1 | 0.1 |
| wheat starch | 3.53 | 3.46 | 2.68 |
| sorbitol | 3.2 | 3.2 | 2.9 |
| water | 45 | 44.6 | 44.7 |
| peppermint oil | 20 drops | 20 drops | 20 drops |

For preparing the aforesaid compositions, a gel is formed by mixing and beating together carragheenan (known as "AUBYGUM $X_2$"), carragheenin and 50% water.

Thereafter, $CaCO_3$, glycerin, $NH_4$-laurylsulfonate, saccharine, methyl p-hydroxybenzoate, wheat starch, sobitol, water and peppermint oil are successively incorporated in this gel.

Compositions A, B and C, thus prepared, comply with the various criteria of consistency, texture, stability, foaming capacity, taste, dispersibility and rinsability which are compulsary for the usual systematic control tests preceeding clinical test.

Bacteriological analyses of compositions A, B, C have also yield satisfactory results; these analyses are in fact of great importance since microbial development may be highly objectionable to the appearance, taste and efficiency of the dentifrice composition.

Composition C has been used in accordance with the test sequence disclosed hereafter for treating an intensive ulcero-necrotic gingivitis in a man 21 years old, this gingivitis being characterized by an initial PMA of 15; after 8 days, PMA has dropped to 3 and after 15 days it was only 1; obviously this treatment has taken place without any antibiotherapy.

Likewise, composition A has been used for treating a gingivitis in a man 25 years old, said gingivitis being characterized by an initial PMA of 14 and said index became 0 after 15 days.

Pharmacological tests 1-test sequence

Dentifrice compositions A, B and C, as well as a placebo composition (i.e., a composition containing no carragheenin) have been placed in randomly-numbered tubes without informing the user or the practitioner, who will have to appraise the results, about the concentration of carragheenin in the respective compositions.

Persons suffering from gingivitis (either known or discovered) have used the composition of the invention or, as the case may be, the placebo composition, as a dentifrice for regular tooth brushing (for 2 minutes), twice a day, the use of any other toothpaste for the whole duration of the treatment being prohibited. The gingivitis lesions have been estimated both initially on each subject by an examination of the oral cavity and, in each case, the absence of bone lesions has been determined by radiography.

The examination of the oral cavity has been effected in each case by the same stomatologist under strictly identical conditions, so as to limit to a minimum the possible margin or error due to the subject character of any appreciation concerning the development of inflammatory phenomenona.

The PMA index has been determined on an arbitrary scale as follows: "1" = papillary attack; "2" = marginal gum attack; and "3" = deeper attack, the results being summed up; the determination of PMA has been effected for the six front teeth of the mandible, that is to say teeth the more accessible for a direct visual examination.

Photographs had also been taken before the treatment, upon initial examination and upon each subsequent examination in order to monitor the evolving of the lesions under the effect of the dentifrice. Such documents have the advantage of being accurate and reproduced very truly the lesions at any given stage; they give the possibility of appreciating the evolving of the lesions with time by comparing pictures taken under absolutely similar conditions as recommended by SCHOUR and MASSLER ("Survey of Gingival diseases using the PMA index" in J. Denters, 27, p. 7322-1948).

Examinations were carried out after 8 days, 15 days and one month treatment. The obtained results are summarised in tables II to V hereafter, wherein the various abbreviations have the following means:

$PMA_i$ = initial PMA index
$PMA_1$ = PMA index after 8 days treatment
$PMA_2$ = PMA index after 15 days treatment
$PMA_3$ = PMA index after 1 month treatment.

TABLE II

Treatment of gingivitis with composition A(0.5% of carragheenin)

| $PMA_i$ | $PMA_1$ | $PMA_2$ | $PMA_3$ |
|---|---|---|---|
| 15 | 3 | 3 | — |
| 12 | 6 | — | — |
| 18 | 12 | — | — |
| 13 | 11 | abs | — |
| 12 | 10 | 11 | — |
| 14 | 11 | — | 11 |
| 14 | abs | 0 | 0 | abs= absent.

TABLE III

Treatment of gingivitis with composition B(1% of carragheenin)

| $PMA_i$ | $PMA_1$ | $PMA_2$ | $PMA_3$ |
|---|---|---|---|
| 9 | 7 | 6 | — |
| 9 | 8 | — | — |
| 10 | 2 | 2 | 2 |

TABLE IV

Treatment of gingivitis with composition C(2% of carragheenin)

| $PMA_i$ | $PMA_1$ | $PMA_2$ | Remarks |
|---|---|---|---|
| 14 | 12 | 12 | — |
| 14 | 10 | — | — |
| 14 | 13 | 10 | — |
| 15 | 3 | 1 | ulcero-necrotic gingivites |
| 8 | 2 | — | — |

TABLE V

| Treatment of gingivitis with placebo composition defined hereunder (carragheenin 0%) | | | |
|---|---|---|---|
| $PMA_i$ | $PMA_1$ | $PMA_2$ | $PMA_3$ |
| 12 | — | 6 | — |
| 10 | — | 6 | — |
| 12 | 10 | 9 | — |
| 11 | 10 | 7 | 7 |
| 13 | 7 | 3 | 3 |

The placebo composition used in this test contains the following components in specify amounts

| (by weight). | |
|---|---|
| Carragheenin | 0 |
| Carragheenan | 1% |
| $CaCO_3$ | 32% |
| Glycerin | 15% |
| $NH_4$ laurylsulfonate | 1.8% |
| Saccharine | 0.1% |
| Methyl-p-hydroxy-benzoate | 0.1% |
| Wheat starch | 3.5% |
| Sorbitol | 2% |
| Water | 44.5% |
| Peppermint | 20 drops. |

The above results show that a decrease of PMA has been obtained during the treatment of gingivitis with compositions of the invention. No aggravation or even no stabilisation has been observed with compositions containing carragheenin. The improvement between the first and the second examinations is always substantial and sometimes even extremely rapid; for an initial PMA of 15 there has been obtained a PMA of 3 upon of the second examination with compositions A or C according to the invention (see tables II and IV).

In table VI thereafter is shown the mean value of PMA indexes obtained in the above test for each composition.

TABLE VI

| Composition | Mean value of PMA | | | |
|---|---|---|---|---|
|  | $PMA_i$ | $PMA_1$ | $PMA_2$ | $PMA_3$ |
| A | 14 | 9 | 7 | — |
| B | 9 | 6 | 4 | 2 |
| C | 13 | 8 | 7 | — |
| placebo | 11.6 | 9 | 6 | 5 |

These results show that placebo compositions have brought a certain improvement due to the fact that the regular brushing of teeth effected during the test has massaged the gums.

However, the above results show that compositions A, B and C of the invention bring a definite improvement of the state of the gums even at concentrations of 0.5% of carragheenin.

During the tests there has been noted no side effects or intolerance.

The tests show that iota carragheenin used in the compositions of the invention has antiinflammatory properties and that compositions of the invention are useful against gingivitis.

Obviously the composition of the invention can be used as a prophylaxis against gingivitis for keeping the gums in a healthy state.

It is to be understood that obvious modifications can be made in the disclosed embodiments, the scope of the invention being defined by the appended claims.

What we claim is:

1. A pharmaceutically-acceptable dentifrice composition having an effective concentration of gingivitis-controlling active ingredient, an essential gingivitis-controlling component of which is at least one carragheenin.
2. A composition according to claim 1 wherein the essential gingivitis-controlling component is present in a concentration of from 0.5 to 25 percent by weight and is in combination with a pharmaceutically-acceptable carrier.
3. A composition according to claim 2 wherein the concentration of the gingivitis-controlling component is from 0.5 to 10 percent by weight.
4. A composition according to claim 1 wherein each carragheenin is a member selected from the group consisting of iota-carragheein, lambda-carragheenin and kappa-carragheenin.
5. A composition according to claim 1 having an abrasive agent, a surface-active agent, a thickener, a sweetener, a flavoring agent and a preservative.
6. A toothpaste composition according to claim 1.
7. Toothpaste composition useful for controlling gingivitis which comprises, by weight, about:
   0.5 to 10% carragheenin
   0.5 to 2% carragheenan
   2 to 4% sorbitol
   25 to 35% light $CaCO_3$
   2 to 4% wheat starch
   1 to 3% surface active agent
   10 to 20% glycerine
   about 0.1% saccharine, about 0.1% methylparahydroxybenzoate and a suitable amount of a flavoring agent, the balance to 100% being water.
8. A toothpaste composition according to claim 7 wherein the surface active agent is a member selected from the group consisting of Na-laurylsulfonate and $NH_4$-laurylsulfonate.
9. A composition according to claim 7 with from 0.5 to 2 percent by weight of carragheenin, from 0.67 to 0.72 percent by weight of carragheenan, 30 percent by weight of light $CaCO_3$, 14.5 percent by weight of glycerin, 2.35 percent by weight of ammonium lauryl-sulfonate, 0.1 percent by weight of saccharine, from 2.68 to 3.53 percent by weight of wheat starch, from 2.9 to 3.2 percent by weight of sorbitol, from 44.6 to 45 percent by weight of water and sufficient peppermint oil for flavoring.
10. A composition according to claim 1 in liquid dentifrice form.
11. A composition according to claim 1 in dental milk form.
12. A composition according to claim 1 in dental powder form.
13. A pharmaceutically-acceptable gingivitis-controlling mouthwash composition having an effective concentration of at least one carragheenin.
14. In a chewing-gum composition having a physiologically-active ingredient therein, the improvement wherein an essential component of the physiologically-active ingredient is at least one carragheenin and the component constitutes a proportion of the composition effective to control gingivitis.
15. A method of controlling gingivitis by contacting affected tissue with an effective concentration of at least one carragheenin.
16. A method of controlling gingivitis by brushing teeth with an effective amount of a tooth-paste composition according to claim 9.

17. A method according to claim 15 consisting of applying to the oral cavity an effective amount of a pharmaceutical composition comprising, as active ingredient 0.5 to 25% by weight of at least one carragheenin in combination with a pharmaceutically-acceptable carrier, said composition being applied for a time sufficient to establish an intimate contact with said oral cavity.

18. A method according to claim 17 wherein the active ingredient in the pharmaceutical composition is selected from iota, lambda and kappa carragheenins and mixtures thereof.

19. Method of treatment adapted to control gingivitis consisting in applying to teeth, by brushing, an effective amount of an anti-gingivitis tooth-paste composition according to claim 6 having, by weight:

0.5 to 10% carragheenin
0.5 to 2% carragheenan
2 to 4% sorbitol
25 to 35% light $CaCO_3$
2 to 4% wheat starch
1 to 3% surface active agent
10 to 20% glycerine about 0.1% saccharine, about 0.1% methyl parahydroxybenzoate and a suitable amount of a flavoring agent, the balance to 100% being water.

* * * * *

UNITED STATES PATENT OFFICE
CERTIFICATE OF CORRECTION

Patent No. 4,029,760          Dated June 14, 1977

Inventor(s)   De Roeck et al

It is certified that error appears in the above-identified patent and that said Letters Patent are hereby corrected as shown below:

On the title page, line 3 of the Abstract, "ingredient" should read --ingredient,--. Column 1, line 46, "later" should read --latter--; line 51, "Riechstoffe"" should read --Riechstoffe",--; line 52, "Janistyn" should read --Janistyn,-- and "Huthig" should read --Huthig,--; line 67, "No10" should read --No. 10--. Column 2, line 3, "be" should read --by--; line 6, "seen" should read --see--; line 7, "cosmetologie" should read --cosmétologie--; line 13, "intenstinal" should read --intestinal--; line 20, "14" should read --*14*--; line 21, "106" should read --*106*--; line 42, "and," should read --and contains,--; line 45, "preservative" should read --preservative,--. Column 3, line 5, "a" should read --an--; line 11, "agent" should read --agents--; line 23, "agents," should read --agents--. Column 4, line 56, "J. Periodant., 1957, 28" should read --*J. Periodant.*, 1957, *28*--. Column 5, approximately line 13, "0.6" should read --0.67--; line 24, "X$_2$" should read --X$_2$"--; line 26, "Thereafter" should not begin a new paragraph; line 33, "compulsary" should read --compulsory--; line 36, "have also" should read --also--. Column 6, line 6, "or" should read --of--; line 27, "J. Denters" should read --*J. Denters*--. Column 7, line 12, "specify amounts" should read --specific amounts (by weight); approximately line 14, delete "(by weight)"; line 28, "or even" should read --or--; line 29, "no stabilisation"

UNITED STATES PATENT OFFICE
CERTIFICATE OF CORRECTION

Patent No. 4,029,760          Dated June 14, 1977

Inventor(s)    De Roeck et al

It is certified that error appears in the above-identified patent and that said Letters Patent are hereby corrected as shown below:

should read --stabilisation--; line 34, "of the" should read --the--.

Signed and Sealed this

Twenty-eighth Day of February 1978

[SEAL]

Attest:

RUTH C. MASON
*Attesting Officer*

LUTRELLE F. PARKER
*Acting Commissioner of Patents and Trademarks*